US008792981B2

(12) United States Patent
Yudovsky et al.

(10) Patent No.: US 8,792,981 B2
(45) Date of Patent: Jul. 29, 2014

(54) OMNIDIRECTIONAL ACCELEROMETER DEVICE AND MEDICAL DEVICE INCORPORATING SAME

(71) Applicant: Medtronic Minimed, Inc., Northridge, CA (US)

(72) Inventors: Dmitry Yudovsky, Los Angeles, CA (US); Ian B. Hanson, Wayne, PA (US); Sheldon B. Moberg, Thousand Oaks, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 13/750,743

(22) Filed: Jan. 25, 2013

(65) Prior Publication Data
US 2013/0133427 A1    May 30, 2013

Related U.S. Application Data

(62) Division of application No. 12/611,341, filed on Nov. 3, 2009, now Pat. No. 8,386,042.

(51) Int. Cl.
*A61N 1/00* (2006.01)

(52) U.S. Cl.
USPC .......................... 607/19; 600/595; 73/514.34

(58) Field of Classification Search
USPC .................. 600/552–553, 587, 595; 604/131; 607/17–19, 21–22, 24, 27; 73/431, 73/493, 514.15, 514.16, 514.21, 514.34, 73/514.36, 514.38; 310/328
See application file for complete search history.

(56) References Cited

U.S. PATENT DOCUMENTS

| 5,088,326 A * | 2/1992 | Wada et al. ................. 73/514.34 |
| 6,338,199 B1 * | 1/2002 | Chigira et al. ................... 33/318 |
| 2006/0217776 A1 * | 9/2006 | White et al. ..................... 607/35 |

* cited by examiner

*Primary Examiner* — Rene Towa
(74) *Attorney, Agent, or Firm* — Ingrassia Fisher & Lorenz, P.C.

(57) ABSTRACT

A portable medical device is provided with an internal accelerometer device. The medical device includes a circuit board, the accelerometer device, and a response module coupled to the accelerometer device. The accelerometer device is mechanically and electrically coupled to the circuit board, and it includes a plurality of mass-supporting arms for a plurality of electrically distinct sensor electrodes, piezoelectric material for the mass-supporting arm, and a proof mass supported by the mass-supporting arms. Each of the mass-supporting arms has one of the sensor electrodes located thereon. Acceleration of the proof mass causes deflection of the piezoelectric material, which generates respective sensor signals at one or more of the sensor electrodes. The response module is configured to initiate an acceleration-dependent operation of the portable medical device in response to generated sensor signals present at the sensor electrodes.

20 Claims, 10 Drawing Sheets

OMNIDIRECTIONAL ACCELEROMETER DEVICE AND MEDICAL DEVICE INCORPORATING SAME

CROSS-REFERENCE TO RELATED APPLICATIONS

This application is a divisional of U.S. patent application Ser. No. 12/611,341 filed on Nov. 3, 2009. The entire disclosure of the above application is incorporated herein by reference.

TECHNICAL FIELD

Embodiments of the subject matter described herein relate generally to accelerometer devices and medical devices that utilize accelerometer devices. More particularly, embodiments of the subject matter relate to a monolithic accelerometer device that is capable of detecting acceleration in an omnidirectional manner.

BACKGROUND

Accelerometers can be found in electronic devices such as handheld video game devices, cellular telephones, pedometers, and portable medical devices. An accelerometer could be used to detect environmental conditions such as vibration, impact, or user activity. An accelerometer could also be used as a control device. For example, some video game devices and controllers incorporate accelerometers (and/or other sensors) that detect motion, orientation, or acceleration, where the detected phenomena can be translated into commands or instructions for the video game. A medical device might utilize one accelerometer to measure physical activity levels of the user and another accelerometer to detect physical impacts or trauma suffered by the medical device. For example, if an onboard accelerometer detects a relatively high physical impact, then the medical device could record the impact event and/or remind the user to inspect the medical device for proper operation.

In a medical device, human activity is typically characterized by relatively low frequency and relatively low amplitude excitation. In contrast, physical impacts are usually associated with relatively high frequency and relatively high amplitude excitation. Furthermore, both excitation modes can be associated with acceleration in any direction and at random or unpredictable times. At this time, no commercially available accelerometer device can effectively handle both excitation modes in a physically small, cost-effective, direction insensitive, and power efficient package.

BRIEF SUMMARY

An embodiment of an omnidirectional accelerometer device is provided. The omnidirectional accelerometer device includes a piezoelectric sensor element and a proof mass. The piezoelectric sensor element has an electrically conductive support substrate, a layer of piezoelectric material overlying the support substrate, and a plurality of electrically conductive sensor electrodes overlying the piezoelectric material. The piezoelectric sensor element also includes a mass-supporting platform and a plurality of mass-supporting arms. Each of the sensor electrodes is located on a corresponding one of the mass-supporting arms, and the proof mass is coupled to the mass-supporting platform.

Also provided is an embodiment of a portable medical device. The portable medical device includes a circuit board and an accelerometer device mechanically and electrically coupled to the circuit board. The accelerometer device includes: a plurality of mass-supporting arms for a plurality of electrically distinct sensor electrodes, each of the mass-supporting arms having one of the sensor electrodes located thereon; piezoelectric material for the mass-supporting arms; and a proof mass supported by the mass-supporting arms, wherein acceleration of the proof mass causes deflection of the piezoelectric material, which generates respective sensor signals at one or more of the sensor electrodes. The portable medical device also includes a response module coupled to the accelerometer device. The response module is configured to initiate an acceleration-dependent operation of the portable medical device in response to generated sensor signals present at the sensor electrodes.

Another embodiment of an omnidirectional accelerometer device is also provided. This embodiment of the accelerometer device includes a piezoelectric sensor element comprising a mass-supporting platform and a plurality of mass-supporting arms for a plurality of electrically distinct sensor electrodes. Each of the mass-supporting arms extends from the mass-supporting platform, and each of the mass-supporting arms has one of the sensor electrodes formed thereon. The accelerometer device also includes a connecting rod having a mounting end, a mass end, and a longitudinal length defined between the mounting end and the mass end, the mounting end being coupled to the mass-supporting platform. The accelerometer device also has a proof mass coupled to the mass end of the connecting rod, wherein acceleration of the proof mass causes deflection of the mass-supporting arms, which generates distinct sensor signals at the sensor electrodes. The longitudinal length of the connecting rod is tuned in accordance with a predetermined parallel acceleration sensitivity for the omnidirectional accelerometer device. Moreover, each of the sensor electrodes has a longitudinal sensor length along its respective mass-supporting arm, and the longitudinal sensor length is tuned in accordance with a predetermined perpendicular acceleration sensitivity for the omnidirectional accelerometer device.

Further provided is an omnidirectional accelerometer device. The omnidirectional accelerometer device includes a piezoelectric sensor element. The piezoelectric sensor element includes a mass-supporting platform and a plurality of mass-supporting arms for a plurality of electrically distinct sensor electrodes. Each of the mass-supporting arms extend from the mass-supporting platform, and each of the mass-supporting arms has one of the sensor electrodes formed thereon. The omnidirectional accelerometer device includes a connecting rod having a mounting end, a mass end, and a longitudinal length defined between the mounting end and the mass end. The mounting end of the connecting rod is coupled to the mass-supporting platform. The omnidirectional accelerometer device also includes a proof mass coupled to the mass end of the connecting rod and adjustable along the longitudinal length of the connecting rod to tune the omnidirectional accelerometer device in accordance with a predetermined parallel acceleration sensitivity. Acceleration of the proof mass causes deflection of the mass-supporting arms, which generates distinct sensor signals at the sensor electrodes.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
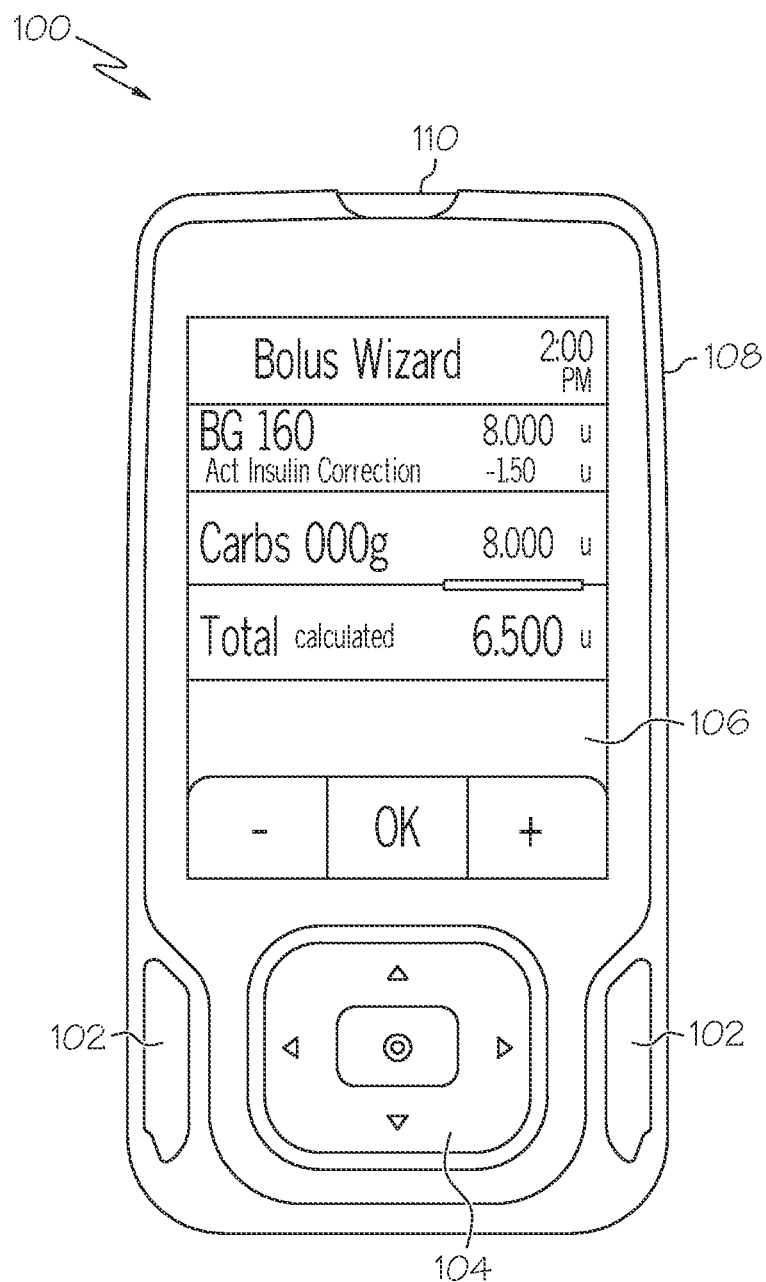
FIG. 1 is a plan view of an exemplary embodiment of a wireless monitor/controller for an infusion pump.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

The following description may refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

In addition, certain terminology may also be used in the following description for the purpose of reference only, and thus are not intended to be limiting. For example, terms such as "upper", "lower", "above", and "below" might refer to directions in the drawings to which reference is made. Terms such as "front", "back", "rear", "side", "outboard", and "inboard" may be used to describe the orientation and/or location of portions of a component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

Medical Device Embodiment

The systems, methods, and technologies described below can be implemented in an electronic device having one or more accelerometer devices incorporated therein. Although the subject matter described here is applicable to any accelerometer-enabled electronic device, the exemplary embodiments are implemented in the form of medical devices, such as portable electronic medical devices. The described medical devices may be associated with a single patient or with multiple patients. The medical devices may be designed to treat one or more different medical conditions, and each medical device might have a specific function in the context of an overall patient treatment or healthcare plan. The non-limiting examples described below relate to a medical device system used to treat diabetes, although embodiments of the disclosed subject matter are not so limited.

The subject matter described here is related to accelerometers and their use with portable electronic devices such as medical devices. Although many different applications are possible, the following description focuses on an infusion system deployment. For the sake of brevity, conventional techniques related to infusion system operation, insulin pump and/or infusion set operation, blood glucose sensing and monitoring, signal processing, data transmission, signaling, network control, and other functional aspects of the systems (and the individual operating components of the systems) may not be described in detail here. Examples of infusion pumps and/or communication options may be of the type described in, but not limited to, U.S. Pat. Nos. 4,562,751; 4,685,903; 5,080,653; 5,505,709; 5,097,122; 6,554,798; 6,558,320; 6,558,351; 6,641,533; 6,659,980; 6,752,787; 6,817,990; and 6,932,584, which are herein incorporated by reference. Examples of glucose sensing and/or monitoring devices maybe be of the type described in, but not limited to, U.S. Pat. Nos. 6,484,045; 6,809,653; 6,892,085; and 6,895,263, which are herein incorporated by reference.

A device in an insulin infusion system represents one non-limiting example of an accelerometer-enabled medical device that can respond, take action, or be controlled using one or more onboard accelerometer devices. An insulin infusion system controls the infusion of insulin into the body of a user, and such a system may include a number of devices that communicate (unidirectional or bidirectional) with each other. For example, one exemplary embodiment of an insulin infusion system might include, without limitation: an insulin infusion pump; at least one physiological characteristic sensor, which may be realized as a continuous glucose sensor transmitter; and one or more wireless controller devices. An insulin infusion system may also include or cooperate with a glucose meter that provides glucose meter data, an infusion set for the insulin infusion pump, and an insulin reservoir (or other means for supplying insulin) for the insulin infusion pump. Moreover, an insulin infusion system may include, cooperate with, or communicate with other devices and subsystems such as, without limitation: a stationary monitor device (e.g., a bedside monitor or a hospital monitor); a vehicle communication system; a wireless-enabled watch that is compatible with the insulin infusion system; etc. Any one (or more) of the devices within an insulin infusion system could leverage the accelerometer designs and related techniques and methodologies presented here.

Figure 2:
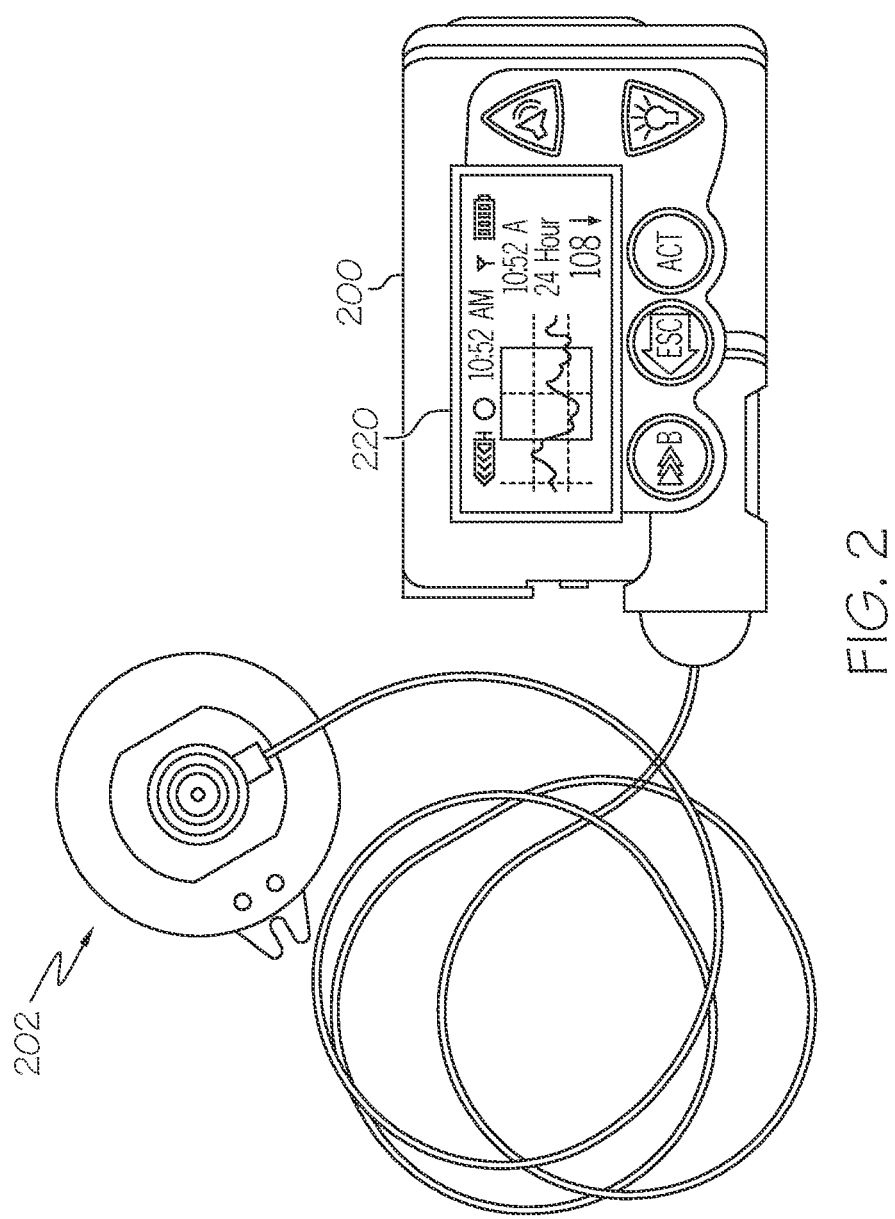
FIG. 2 is a plan view of an exemplary embodiment of an infusion pump and a related infusion set.

FIG. 1 is a plan view of an exemplary embodiment of a wireless monitor/controller 100 for an infusion pump, and FIG. 2 is a plan view of exemplary embodiments of an infusion pump 200 and a related infusion set 202. In practice, the components of an insulin infusion system can be realized using different platforms, designs, and configurations, and the embodiments shown in FIG. 1 and FIG. 2 are not exhaustive or limiting. Moreover, as mentioned previously, other devices in an infusion system, other medical devices designed to address other patient needs, and other portable electronic devices could utilize the accelerometer device presented here. The wireless monitor/controller 100 and the infusion pump 200 are merely two exemplary embodiments.

Referring now to FIG. 1, the wireless monitor/controller 100 is designed as a portable device that can be carried or worn by a user. This particular embodiment includes a human-machine interface (HMI) that includes buttons 102 and a directional pad 104 that can be manipulated by the user. This embodiment also employs a touch screen display element 106 that is responsive to touching and/or physical proximity of an object. The touch screen display element 106 can be used to present various types of information or data to the user, such as, without limitation: the current glucose level of the patient; the time; a graph or chart of the patient's glucose level versus time; device status indicators; alert messages; visual alert indicators; etc.

The buttons 102, directional pad 104, and touch screen display element 106 can be used to administer a bolus of insulin, to change therapy settings, to change user preferences, to select display features, to set or disable alarms and reminders, and the like. As described in more detail below, one or more of these functions could alternatively (or additionally) be controlled via an onboard accelerometer device that is contained within the outer housing 108 of the wireless monitor/controller 100. Depending upon the configuration settings, options, and/or user preferences, the wireless monitor/controller 100 can be manipulated using the buttons 102 only, the touch screen display element 106 only, an onboard accelerometer device, or any combination thereof.

Although not clearly depicted in FIG. 1, the wireless monitor/controller 100 may include a number of features, devices, and/or elements that support alerting or alarm schemes. In this regard, the wireless monitor/controller 100 can be provided with one or more alert generating elements that provide feedback to the user as needed during operation of the wireless monitor/controller 100. An alert generating element may be suitably configured to generate one or more types of feedback, such as, without limitation: audible feedback; visual feedback; haptic (physical) feedback; or the like. Such feedback can be produced by one or more devices, elements, or features of the wireless monitor/controller 100. For example, the wireless monitor/controller 100 may include any number of the following alert generating elements, without limitation: an audio transducer or speaker 110; a display element (such as the touch screen display element 106); a light-emitting element (such as an LED); a haptic feedback or vibration element, which may be integrated into a display screen or into the touch screen display element 106; etc.

Referring now to FIG. 2, the infusion pump 200 is configured to deliver insulin into the body of the patient via, for example, the infusion set 202. In this regard, the infusion pump 200 may cooperate with an insulin reservoir, which can be a replaceable or refillable fluid reservoir for the insulin. In certain embodiments, the infusion pump 200 and/or the wireless monitor/controller 100 can process received glucose sensor data in an appropriate manner. For example, a device might display the current glucose level derived from the received sensor data and/or generate an alert or otherwise indicate low or high glucose levels. As another example, a device may process the received sensor data for purposes of calibration. As yet another example, the infusion pump 200 may be configured to activate its infusion mechanism in response to the received glucose sensor data.

The illustrated embodiment of the infusion pump 200 is designed to be carried or worn by the patient. This particular embodiment includes a human-machine interface (HMI) that includes several buttons that can be activated by the user. These buttons can be used to administer a bolus of insulin, to change therapy settings, to change user preferences, to select display features, and the like. As described in more detail below, one or more of these functions could alternatively (or additionally) be controlled via an onboard accelerometer device. Although not required, the illustrated embodiment of the infusion pump 200 includes a display element 220. The display element 220 can be used to present various types of information or data to the user, such as, without limitation: the current glucose level of the patient; the time; a graph or chart of the patient's glucose level versus time; device status indicators; visual alerts, alarms, reminders, or notifications; etc. In some embodiments, the display element 220 is realized as a touch screen display element. Moreover, the infusion pump 200 could include one or more alert generation elements that support various alarm/alert schemes. In this regard, the relevant description of the alert/alarm related features and functions of the wireless monitor/controller 100 also applies in an equivalent manner to the infusion pump 200, and such description will not be repeated here for the infusion pump 200.

Figure 3:
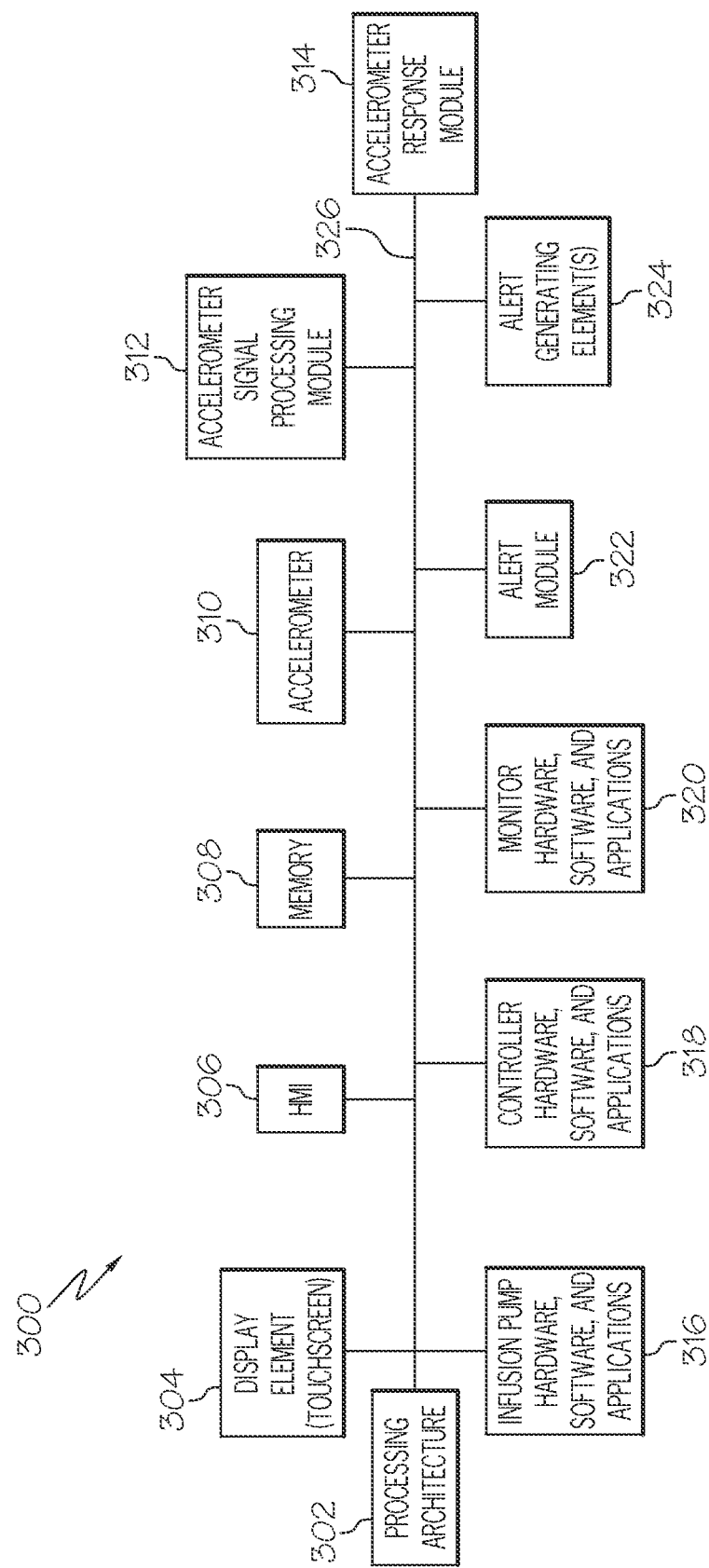
FIG. 3 is a schematic representation of a medical device, which may be realized as an infusion pump, a controller device, or a monitor device.

FIG. 3 is a schematic representation of a medical device 300, which may be realized as an infusion pump, a therapy delivery device, a monitor, or a controller device suitable for use in a medical device system. The illustrated embodiment of the medical device 300 represents a "full-featured" version; a practical embodiment need not include all of the features, modules, components, and elements depicted in FIG. 3.

This particular embodiment of the medical device 300 generally includes, without limitation: a processing architecture 302, processor, or processor arrangement; a display element 304; at least one human-machine interface (HMI) element 306; a suitable amount of memory 308; an accelerometer device 310; an accelerometer signal processing module 312; an accelerometer response module 314; infusion pump hardware, software, and applications 316 (included if the medical device 300 includes infusion pump functionality, and omitted if the medical device 300 does not include infusion pump functionality); controller hardware, software, and applications 318 (included if the medical device 300 includes controller functionality, and omitted if the medical device 300 does not include controller functionality); monitor hardware, software, and applications 320 (included if the medical device 300 includes monitor functionality, and omitted if the medical device 300 does not include monitor functionality); an alert module 322; and one or more alert generating elements 324. The elements of the medical device 300 may be coupled together via a bus 326 or any suitable interconnection architecture or arrangement that facilitates transfer of data, commands, power, etc.

Those of skill in the art will understand that the various illustrative blocks, modules, circuits, and processing logic described in connection with the medical device 300 (and other devices, elements, and components disclosed here) may be implemented in hardware, computer software, firmware, a state machine, or any combination of these. To clearly illustrate this interchangeability and compatibility of hardware, firmware, and software, various illustrative components, blocks, modules, circuits, and processing steps may be described generally in terms of their functionality. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting.

The processing architecture 302 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. A processor device may be realized as a microprocessor, a controller, a microcontroller, or a state machine. Moreover, a processor device may be implemented as a combination of computing devices, e.g., a combination of a digital signal processor and a microprocessor, a plurality of microprocessors, one or more microprocessors in conjunction with a digital signal processor core, or any other such configuration.

The processing architecture 302 may include one processor device or a plurality of cooperating processor devices. Moreover, a functional or logical module/component of the medical device 300 might actually be realized or implemented with the processing architecture 302. For example, the accelerometer signal processing module 312, the accelerometer response module 314, and/or the alert module 322 may be implemented in, or be executed by, the processing architecture 302.

The display element 304 represents a primary graphical interface of the medical device 300. The display element 304 may leverage known CRT, plasma, LCD, TFT, and/or other display technologies. The actual size, resolution, and operating specifications of the display element 304 can be selected to suit the needs of the particular application. Notably, the display element 304 may include or be realized as a touch screen display element that can accommodate touch screen techniques and technologies. In practice, the display element 304 could be used to display physiological patient data, status information for infusion pumps, status information for continuous glucose sensor transmitters, clock information, alarms, alerts, and/or other information and data received or processed by the medical device 300.

HMI elements 306 represent the user interface features of the medical device 300. Thus, HMI elements 306 may include a variety of items such as, without limitation: a keypad, keys, buttons, a keyboard, switches, knobs (which may be rotary or push/rotary), a touchpad, a microphone suitably adapted to receive voice commands, a joystick, a pointing device, an alphanumeric character entry device or touch element, a trackball, a motion sensor, a lever, a slider bar, a virtual writing tablet, or any device, component, or function that enables the user to select options, input information, or otherwise control the operation of the medical device 300. As will become apparent from the following description, the accelerometer device 310 could also serve as an HMI element in certain situations. The medical device 300 can detect manipulation of, or interaction with, the HMI elements 306 and react in an appropriate manner. For example, a user could interact with the HMI elements 306 to control the delivery of therapy (e.g., insulin infusion) to a patient via a therapy delivery device under the control of the medical device 300.

The memory 308 may be realized as RAM memory, flash memory, EPROM memory, EEPROM memory, registers, a hard disk, a removable disk, a CD-ROM, or any other form of storage medium known in the art. In this regard, the memory 308 can be coupled to the processing architecture 302 such that the processing architecture 302 can read information from, and write information to, the memory 308. In the alternative, the memory 308 may be integral to the processing architecture 302. As an example, the processing architecture 302 and the memory 308 may reside in an ASIC. A functional or logical module/component of the medical device 300 might be realized using program code that is maintained in the memory 308. For example, the accelerometer signal processing module 312, the accelerometer response module 314, and/or the alert module 322 may have associated software program components that are stored in the memory 308. Moreover, the memory 308 can be used to store data utilized to support the operation of the medical device 300, as will become apparent from the following description.

The accelerometer device 310 functions to measure the acceleration it experiences. Such acceleration may be caused by motion, shaking, or user handling of the medical device 300, physical activity of the user, impacts caused by handling or dropping the medical device 300, or the like. The embodiments of the accelerometer device 310 described below are omnidirectional in that they are capable of sensing acceleration in all directions. Moreover, certain embodiments of the accelerometer device 310 utilize a monolithic sensor element that can be fabricated easily and in a cost-efficient manner. In practice, the accelerometer device 310 is realized as an integrated component of the medical device 300, and the accelerometer device 310 can be protected within the outer housing of the medical device 300.

The accelerometer signal processing module 312 is coupled to the accelerometer device 310 such that it can receive and process the raw sensor signals that are generated by the accelerometer device 310. The accelerometer signal processing module 312 may include or operate with any number of signal processing sub-modules that are suitably configured to process the accelerometer sensor signals in an appropriate manner to support the various functions and features of the medical device 300. For example, the accelerometer signal processing module 312 may include or cooperate with a first signal processing sub-module that processes the sensor signals for human activity monitoring, and a second signal processing sub-module that processes the sensor signals for impact detection purposes.

In certain implementations, the accelerometer signal processing module 312 generates control signals, commands, or instructions in response to the accelerometer sensor signals. These control signals, commands, or instructions can then be provided to the accelerometer response module 314, which reacts in an appropriate manner. For example, the accelerometer response module 314 may be configured to initiate an acceleration-dependent operation of the medical device 300 in response to the sensor signals generated by the accelerometer device 310. In this regard, the accelerometer response module 314 could initiate an alert operation when the accelerometer signal processing module 312 determines that the accelerometer device 310 has been subjected to an impact that exceeds a designated impact threshold. This feature can be used to notify the user or a technician when the medical device 300 has been dropped or otherwise subjected to a potentially damaging impact. If the accelerometer signal processing module 312 is designed to generate an estimated human activity metric based on the accelerometer sensor signals, then the accelerometer response module 314 could initiate a function that is influenced by the human activity metric. For example, if the accelerometer signal processing module 312 detects a significant amount of physical activity, then the accelerometer response module 314 might initiate certain monitoring functions, initiate delivery of therapy, initiate an adjustment of infusion parameters, or the like.

The infusion pump hardware, software, and applications 316 are utilized to carry out features, operations, and functionality that might be specific to an insulin pump implementation. Again, the infusion pump hardware, software, and applications 316 need not be deployed if the medical device 300 does not include infusion pump functionality. Notably, the infusion pump hardware, software, and applications 316 may include or cooperate with an infusion set and/or a fluid reservoir (not shown). The infusion pump hardware, software, and applications 316 may leverage known techniques to carry out conventional infusion pump functions and operations, and such known aspects will not be described in detail here.

The controller hardware, software, and applications 318 are utilized to carry out features, operations, and functionality that might be specific to a medical device controller implementation. Again, the controller hardware, software, and applications 318 need not be deployed if the medical device 300 is realized as a medical device having no native control capabilities. The controller hardware, software, and applications 318 may leverage known techniques to carry out conventional controller device functions and operations, and such known aspects will not be described in detail here.

The monitor hardware, software, and applications 320 are utilized to carry out features, operations, and functionality that might be specific to a medical device monitor implementation. The monitor hardware, software, and applications 320 need not be deployed if the medical device 300 is realized as a medical device having no native monitor capabilities. The monitor hardware, software, and applications 320 may leverage known techniques to carry out conventional monitor device functions and operations, and such known aspects will not be described in detail here.

The alert module 322 is suitably configured to detect alert conditions, alarm conditions, notification conditions, reminder conditions, and/or other conditions that trigger or otherwise prompt the medical device 300 to generate corresponding alerts, alarms, notifications, reminders, flags, or the like. In certain embodiments, the conditions detected by the alert module 322 are associated with the operation, status, state, functionality, or characteristics of the medical device 300. Thus, the alert module 322 could be suitably configured to detect one or more of the following conditions, without limitation: low BG level; high BG level; insulin reservoir low; replace infusion set; low battery; alarm clock; user-entered reminder; or the like. In certain embodiments, the alert module 322 cooperates with the accelerometer device 310, the accelerometer signal processing module 312, and the accelerometer response module 314 to respond to detected physical activity and/or detected physical impacts. The conditions detected by the alert module 322 could also be associated with the operation, status, state, functionality, or characteristics of another device, system, or subsystem that communicates with the medical device 300. Alternatively (or additionally), the conditions detected by the alert module 322 could be associated with a user or an operator of the medical device 300 (or a user or operator of a device that communicates with the medical device 300). Alternatively (or additionally), the conditions detected by the alert module 322 could be associated with user-entered information, e.g., personal reminders, notes, etc.

The alert generating elements 324 can execute an alerting scheme for an alert condition, under the control of the alert module 322. In practice, the preferred alerting scheme for a given alert, alarm, reminder, or notification may involve one alert generating element 324 (e.g., a speaker) or a plurality of different alert generating elements 324 (e.g., a speaker and a display). Depending upon the implementation, the medical device 300 might employ one or more of the following types of alert generating elements 324, individually or in any combination, and without limitation: an audio transducer or speaker; a display element (such as a touch screen display element); a light-emitting element (such as an LED); a haptic feedback or vibration element, which may be integrated into a display screen or into the touch screen display element; etc.

Monolithic Omnidirectional Accelerometer Device—Design

Accelerometers in wearable medical devices are typically used for at least two functions: human activity monitoring and the detection of potentially damaging impact to the host medical device. Exemplary embodiments of the subject matter described here relate to the mechanical and electrical principles and design of an accelerometer device that can perform both human activity monitoring and impact detection for a portable medical device. Power and space efficiency is realized using certain materials and geometries for the accelerometer device components. Furthermore, the accelerometer device can be implemented such that it has equal (or virtually equal) sensitivity to acceleration in all directions. Such omnidirectionality is desirable for a wearable medical device that can be physically oriented in various directions depending upon how the user wears (or carries) it, and depending upon the physical positioning of the user. Moreover, signal conditioning and processing for the accelerometer device is such that asynchronous events such as impact can be captured without requiring constant monitoring of the accelerometer output signals.

An embodiment of the accelerometer device described here can be manufactured in a cost effective manner and with a monolithic design, a small footprint, and a low profile, which is appropriate for portable or wearable medical device deployments. An embodiment of the accelerometer device described here can also be implemented in a power efficient manner. This feature is desirable for portable medical devices that have very tight power budget constraints (because such medical devices may need to perform reliably without powering down for days or weeks at a time). In this regard, the accelerometer device employs passive signal generation (due to its use of a piezoelectric element). In addition, the accelerometer device could utilize an analog signal buffer that reduces microprocessor use and, consequently, reduces power consumption.

Figure 4:
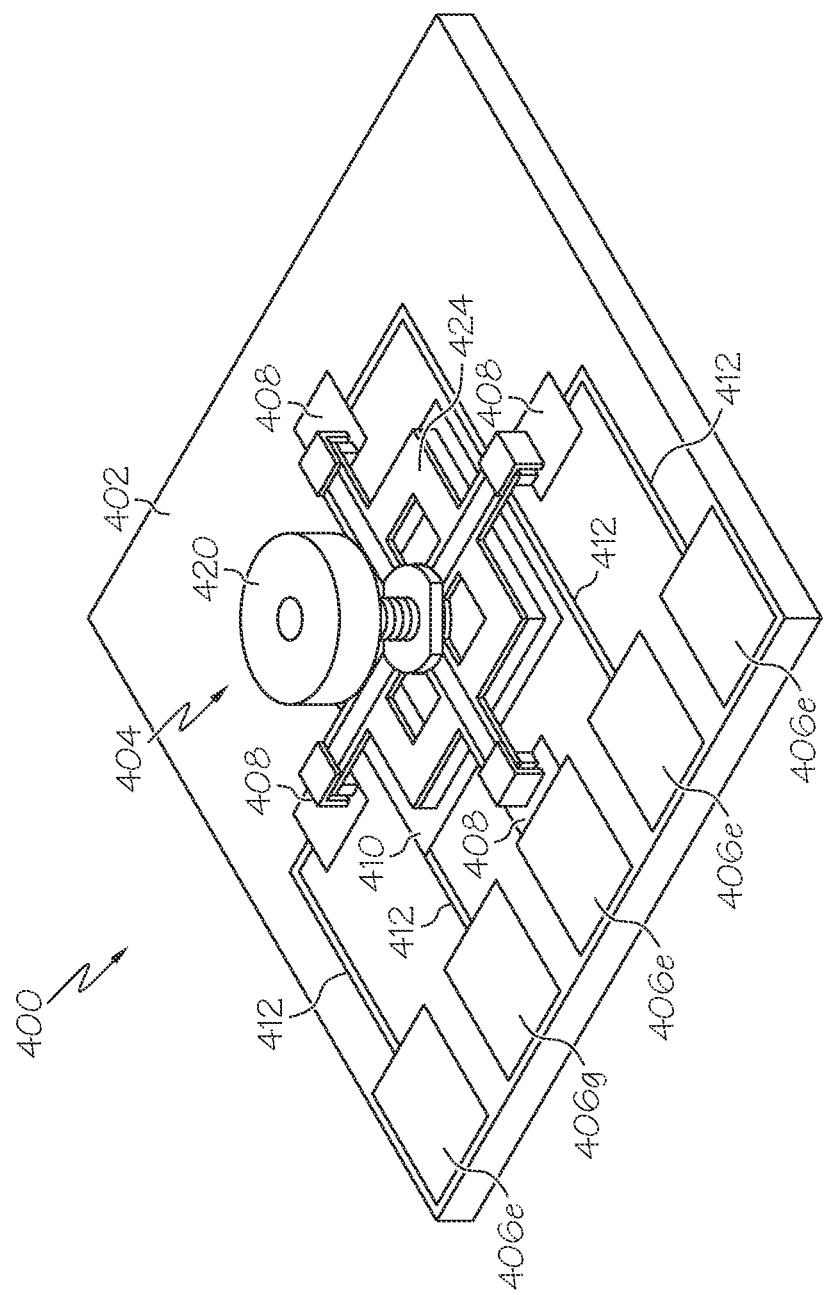
FIG. 4 is a perspective view of an exemplary embodiment of an accelerometer assembly that is suitable for use with a portable medical device.
Figure 5:
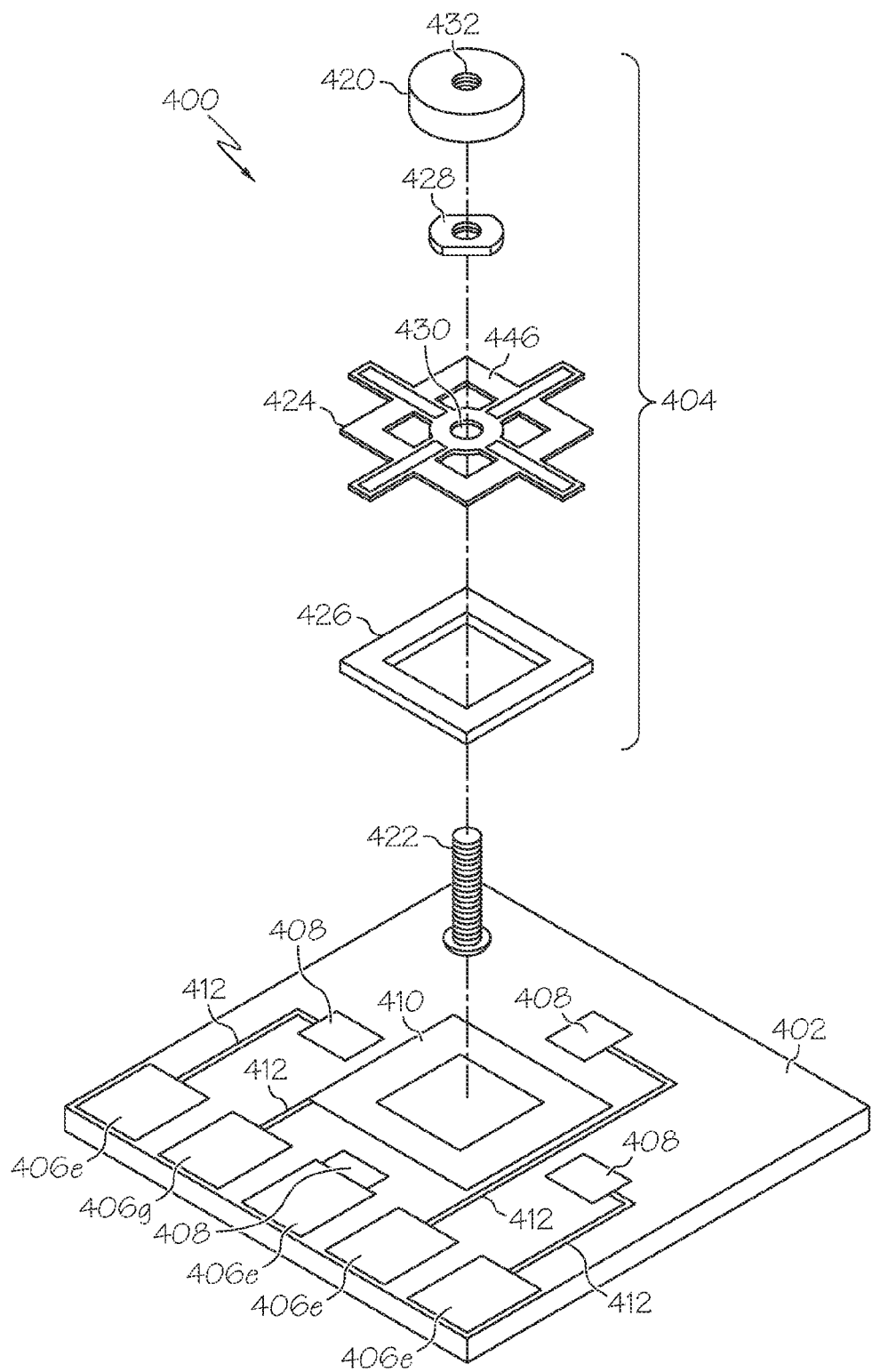
FIG. 5 is an exploded perspective view of the accelerometer assembly shown in FIG. 4.
Figure 6:
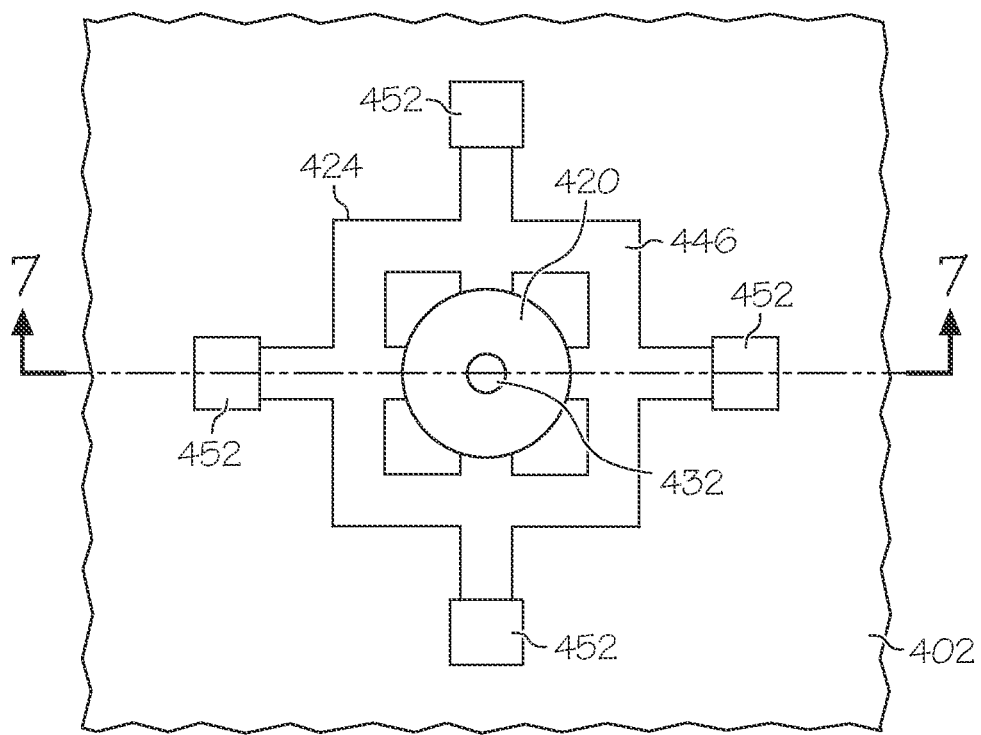
FIG. 6 is a top view of a portion of the accelerometer assembly shown in FIG. 4.
Figure 7:
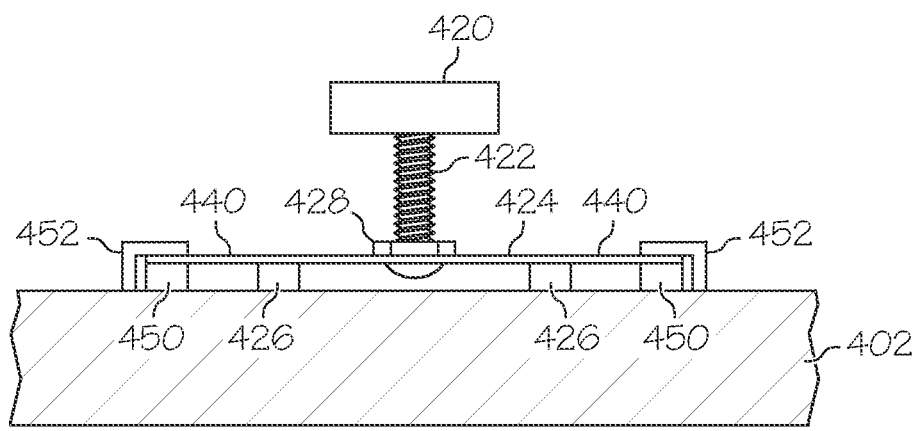
FIG. 7 is a cross-sectional view of the accelerometer assembly as viewed along line 7-7 in FIG. 6.

FIG. 4 is a perspective view of an exemplary embodiment of an accelerometer assembly 400 that is suitable for use with a portable medical device, FIG. 5 is an exploded perspective view of the accelerometer assembly 400, FIG. 6 is a top view of a portion of the accelerometer assembly 400, and FIG. 7 is a cross-sectional view of the accelerometer assembly 400 as viewed along line 7-7 in FIG. 6. The accelerometer device 310 depicted in FIG. 3 could be implemented using the accelerometer assembly 400. This particular embodiment of the accelerometer assembly 400 includes a circuit board 402 and an accelerometer device 404 that is mechanically and electrically coupled to the circuit board 402. The circuit board 402 is formed in accordance with conventional techniques and technologies. For instance, the circuit board 402 could be realized using common FR-4 or similar substrates. This embodiment of the accelerometer assembly 400 uses five electrical contact ports 406 on the circuit board 402: one contact port 406e for each sensor electrode and one contact port 406g for electrical ground. The circuit board 402 may also include a printed conductor and/or a printed contact pad (which may be located on the surface of the circuit board 402 or embedded within the circuit board 402) corresponding to each contact port 406. This embodiment has four contact pads 408 (one for each sensor electrode), and one ground contact pad 410. In addition, this embodiment includes four printed conductors 412 that provide conductive paths to their respective contact ports 406.

The accelerometer device 404 is electrically and mechanically coupled to the circuit board 402 at a number of locations, namely, at or near each of the four contact pads 408 and at or near the ground contact pad 410. In practice, the accelerometer device 404 could be attached to the circuit board 402 using an electrically conductive adhesive, solder, welding agent, bonding agent, or the like. Alternatively (or additionally), fasteners, a press-fit engagement, clamps, or other mechanisms or features could be used to electrically and mechanically couple the accelerometer device 404 to the circuit board 402. The electrical connections are used to obtain the raw sensor signals from the accelerometer device 404 and to route those signals to, for example, the accelerometer signal processing module.

Referring to FIGS. 5-7, the illustrated embodiment of the accelerometer device 404 has a proof mass 420; a connecting rod 422; and a piezoelectric sensor element 424. The accelerometer device 404 may also employ an electrically conductive offset block 426 and a fastener 428. The connecting rod 422 mechanically couples the proof mass 420 to the piezoelectric sensor element 424 and holds the proof mass 420 above the surface of the piezoelectric sensor element 424 at a specified height. In certain embodiments, the connecting rod 422 is realized as a threaded bolt having a mounting end, a mass end, and a longitudinal length that is defined between the mounting end and the mass end. The connecting rod 422 is installed by passing it through a hole 430 formed in the piezoelectric sensor element 424, such that the mounting end of the connecting rod 422 is coupled to the piezoelectric sensor element 424. The fastener 428 (e.g., a lock nut) can then be threaded onto the connecting rod 422 until the connecting rod 422 is secured to the piezoelectric sensor element 424 (see FIG. 6).

The proof mass 420 may have a threaded hole 432 that can be threaded onto the mass end of the connecting rod 422. Thus, the proof mass 420 can be threaded onto the connecting rod 422 until the proof mass 420 reaches the desired height. If necessary, the proof mass 420 can be secured in place on the connecting rod 422 using an adhesive, a bonding agent, a weld, solder, or the like. In practice, the proof mass 420 may be within the range of about 0.05 to 0.15 grams, although the specific quantity of mass could be more or less, depending upon the embodiment. The proof mass 420 could be fabricated from a variety of materials, depending upon the embodiment and the application. For example, the proof mass 420 could be formed from aluminum, copper, brass, stainless steel, tungsten, plastic, rubber, ceramic, or the like.

Figure 8:
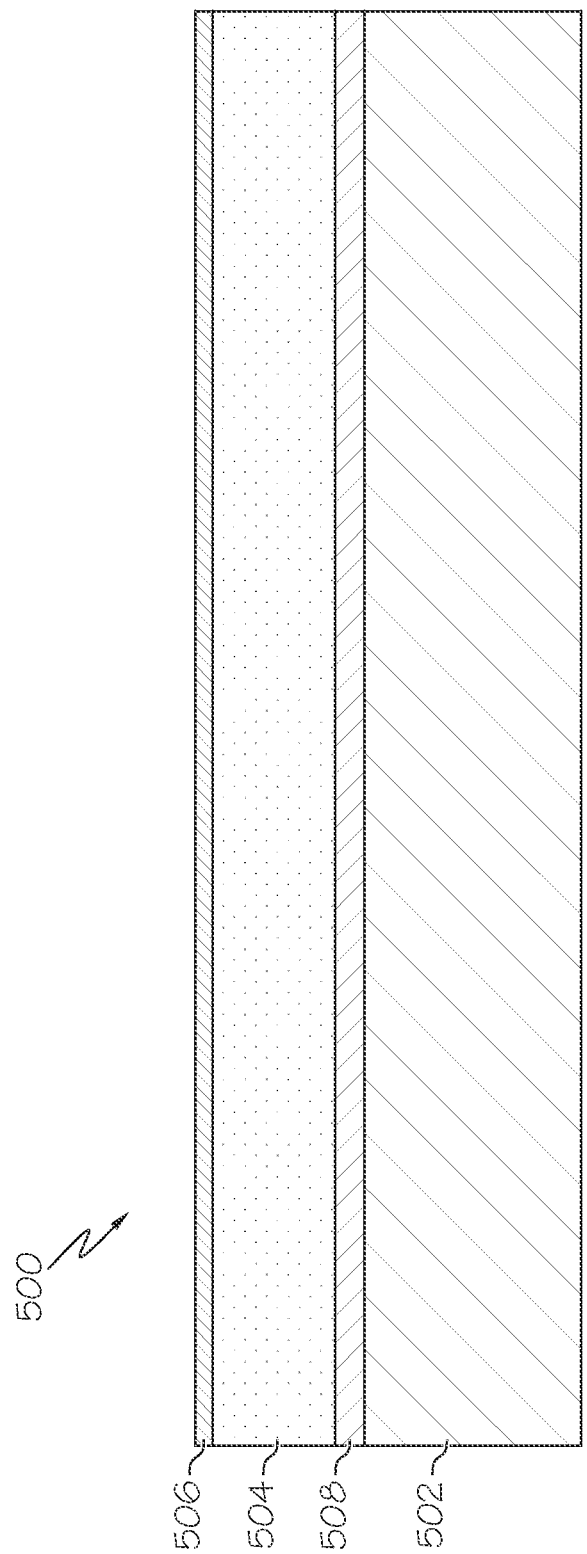
FIG. 8 is a cross-sectional view of an exemplary substrate from which a piezoelectric sensor element can be formed.

The piezoelectric sensor element 424 is fabricated as a monolithic component having a plurality of different material layers. FIG. 8 is a cross-sectional view of an exemplary substrate 500 from which the piezoelectric sensor element 424 can be formed. The illustrated substrate 500 includes an electrically conductive support substrate 502, a layer of piezoelectric material 504 overlying the support substrate 502, and an electrically conductive electrode material 506 overlying the piezoelectric material 504. The support substrate 502 is formed from a relatively stiff and electrically conductive material, such as a beryllium copper material, an aluminum material, or the like. In certain embodiments, the support substrate 502 has a thickness within the range of about 0.025 mm to about 0.050 mm, although the thickness could be more or less, depending upon the implementation.

The piezoelectric material 504 generates an electric potential or charge in response to mechanical stress applied thereto, as is well understood. The piezoelectric material 504 can be, for example, a polyvinylidene fluoride (PVDF) material, or any material with similar piezoelectric properties. In certain embodiments, the piezoelectric material 504 is realized as a thin sheet that is bonded, glued, or otherwise adhered to the support substrate 502. For example, the piezoelectric material 504 could be a sheet of PVDF material having a thickness within the range of about 9 µm to about 110 µm, although the actual thickness may be more or less, depending upon the embodiment. A layer of epoxy 508 or other adhesive or bonding agent can be used to affix the piezoelectric material 504 to the support substrate 502. In practice, epoxy (or any suitable adhesive) can be applied between the piezoelectric material 504 and the support substrate 502, and the assembly can then be heat pressed to adhere the piezoelectric material 504 onto the support substrate 502. Thereafter, the conductive electrode material 506 can be formed overlying the piezoelectric material 504. In certain embodiments, the conductive electrode material 506 is a metal material that is deposited (for example, by sputtering) onto the exposed surface of the piezoelectric material 504. The metal used for the conductive electrode material 506 may be silver, gold, or the like, and the conductive electrode material 506 has a thickness within the range of about 1 µm to about 10 µm (although the actual thickness could be outside this typical range, depending upon the embodiment). The substrate 500 depicted in FIG. 8 is obtained after deposition of the conductive electrode material 506.

After fabricating the substrate 500, the layer of conductive electrode material is processed to form a plurality of electrically conductive sensor electrodes overlying the piezoelectric material 504. The sensor electrodes can be formed by laser etching a desired pattern into the conductive electrode material 506, by selective chemical etching, or the like. For this particular embodiment, the conductive electrode material 506 is selectively removed while the underlying piezoelectric material 504 remains intact. As a result of this processing step, separate and distinct electrical sensing nodes are created for the piezoelectric sensor element. In other words, each of the plurality of sensor electrodes can serve as an independent sensor for the accelerometer device. After the sensor electrodes have been created, the substrate 500 can be stamped, cut, or otherwise processed to form the piezoelectric sensor element.

Figure 9:
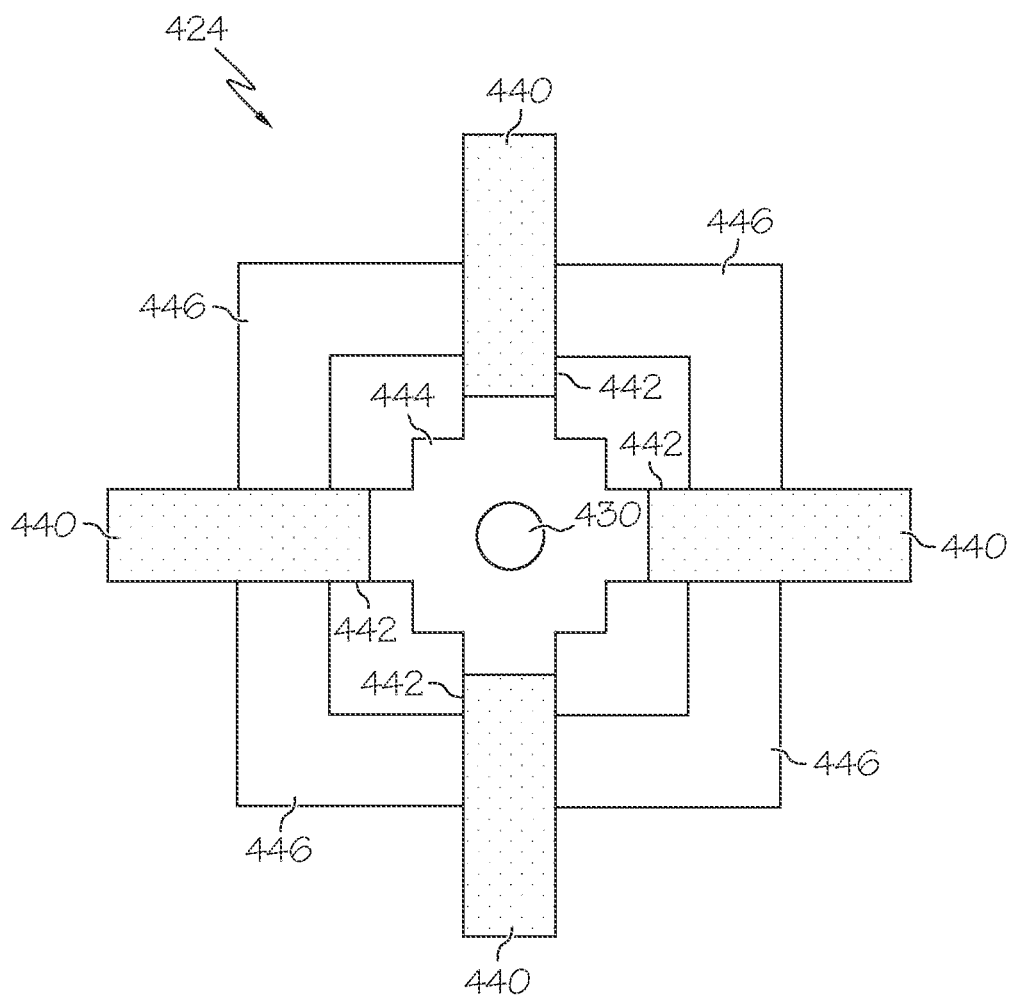
FIG. 9 is a top view of an exemplary embodiment of a piezoelectric sensor element.

FIG. 9 is a top view of an exemplary embodiment of the piezoelectric sensor element 424. This piezoelectric sensor element 424 includes four electrically conductive sensor electrodes 440, which overlie the piezoelectric material (not shown in FIG. 9). Each of the sensor electrodes 440 is located on a respective mass-supporting arm 442 of the piezoelectric sensor element 424. The mass-supporting arms 442 extend from a mass-supporting platform 444 of the piezoelectric sensor element 424. For this embodiment, any two adjacent mass-supporting arms 442 are orthogonal, the four mass-supporting arms 442 form a symmetric pattern, and all of the mass-supporting arms 442 have the same dimensions. In certain embodiments, the length of each mass-supporting arm 442 is within the range of about 1 mm to about 1.6 mm, although other lengths could be used depending on the desired application. Although adjacent mass-supporting arms 442 are orthogonal here, they could be configured to define any chosen separation angle for the piezoelectric sensor element 424. Notably, the sensor electrodes 440 are electrically and physically distinct and separate from one another. In other words, no two sensor electrodes 440 are directly electrically connected together. Consequently, the upper surface of the mass-supporting platform 444 (i.e., the area void of stippling as depicted in FIG. 9) is non-conductive in this embodiment.

Although the exemplary embodiment utilizes four mass-supporting arms 442 (for ease of production and assembly), any number of mass-supporting arms and respective sensor electrodes could be used, as long as that number is greater than or equal to three. In this regard, three mass-supporting arms and three corresponding sensor electrodes is the minimum number required to obtain three-axis sensitivity.

The piezoelectric sensor element 424 includes the hole 430 formed in the mass-supporting platform 444. As mentioned above with reference to FIG. 5, the hole 430 serves as a mounting hole for the mounting end of the connecting rod 422 (not shown in FIG. 9). Thus, the mass-supporting platform 444 holds and supports the proof mass 420 above the piezoelectric sensor element 424. Accordingly, the proof mass 420 will be centrally located relative to the mass-supporting arms 442, and the mass-supporting arms 442 will be symmetrically positioned relative to the proof mass 420. This particular embodiment includes a support structure 446, which resembles a square-shaped ring. This support structure 446 may be desirable to provide additional rigidity and mechanical support to the mass-supporting arms 442. The size of the support structure 446 may also be reduced to save space by removing some or all material that is not directly below the film. In operation, acceleration of the proof mass 420 causes deflection of the piezoelectric material, which in turn generates respective sensor signals at one or more of the sensor electrodes 440. The stiffness (e.g., the modulus of elasticity) of the piezoelectric sensor element 424 will influence the sensitivity of the accelerometer device 404. In practice, the modulus of elasticity of the piezoelectric sensor element 424 could be within the range of about 100 Gpa to about 200 Gpa, although the modulus could be more or less, depending upon the specific implementation. Again, since four sensor electrodes 440 are utilized in this implementation, acceleration of the proof mass 420 can generate four distinct and detectable sensor signals. The sensor signals produced by the stressing of the piezoelectric material can be detected, monitored, and processed in the manner described in more detail below.

Referring again to FIGS. 4-7, the piezoelectric sensor element 424 is electrically and mechanically coupled to the circuit board 402 such that the sensor signals generated by the piezoelectric sensor element 424 can be detected and processed. In this embodiment, the electrically conductive offset block 426 couples the conductive support substrate of the piezoelectric sensor element 424 to the ground contact pad 410 of the circuit board 402 (see FIG. 4). The offset block 426 is formed from an electrically conductive material such as copper, aluminum, beryllium copper, a plated ceramic, or the like. The piezoelectric sensor element 424 and the offset block 426 can be soldered, bonded, fastened, clamped or otherwise attached to the ground contact pad 410 to form an electrically conductive junction and to mechanically attach them together. In operation, the offset block 426 and the conductive support substrate of the piezoelectric sensor element 424 correspond to a reference voltage (e.g., ground or zero volts DC), which is established via the electrical ground contact port 406g. The offset block 426 may also serve to physically maintain the piezoelectric sensor element 424 above the surface of the circuit board 402 to provide clearance for the mounting end of the connecting rod 422 (see FIG. 7).

The ground plane of the piezoelectric sensor element 424 is located on its lower surface (see FIG. 7 and FIG. 9). Each sensor electrode 440 is located on the upper surface of a respective mass-supporting arm 442 of the piezoelectric sensor element 424, and each sensor electrode 440 corresponds to a respective sensor signal voltage. The illustrated embodiment employs an electromechanical mounting arrangement that is configured to mechanically and electrically couple the sensor electrodes 440 to the circuit board 402 (see FIG. 6 and FIG. 7). The illustrated embodiment of the mounting arrangement includes a plurality of electrically conductive mounting bases 450 (one for each sensor electrode 440) and a plurality of electrically conductive mounting tabs 452 (one for each sensor electrode 440). The mounting bases 450 could be realized as surface mount components, and electrically conductive epoxy or solder could be used to mechanically and electrically join the mounting bases 450 and the mounting tabs 452 to their respective locations on the piezoelectric sensor element 424. Alternatively, the mounting bases 450 and mounting tabs 452 could be realized as clamping or press-fit components that need not rely on other material (such as epoxy or solder). As shown in FIG. 7, each sensor electrode 440 of a respective mass-supporting arm 442 is mechanically and electrically coupled to the circuit board 402 with one of the mounting bases 450 and one of the mounting tabs 452. The mounting bases 450 are electrically coupled to the conductive support substrate of the piezoelectric sensor element 424, and each mounting tab 452 is electrically coupled to a respective one of the sensor electrodes 440.

The mounting bases 450 can be electrically coupled to the ground contact port 406g using conductive traces in the circuit board 402. The mounting tabs 452 can be electrically coupled to a respective one of the contact pads 408 and, in turn, to a respective one of the electrode contact ports 406e (see FIG. 4). Thus, the sensor signal potential for each sensor electrode 440 will be present at its respective electrode contact port 406e on the circuit board 402. The accelerometer signal processing module 312 (see FIG. 3) and/or other modules of the host electronic device can be connected to the contact ports 406 to access, monitor, or process the sensor signals as needed.

Accelerometer Sensitivity Tuning

The sensitivity of the accelerometer device 404 can be tuned by changing certain electrical, mechanical, or other characteristics of its components. For example, it might be desirable to tune the sensitivity such that the accelerometer device 404 has equal sensitivity in all directions. Alternatively, it may be desirable to tune the accelerometer device 404 such that it is more or less sensitive in designated directions, relative to other directions.

As one tuning example, the overall major axis length of the connecting rod 422 can be selected or defined in accordance with a predetermined parallel acceleration sensitivity for the accelerometer device 404. In this context, "parallel acceleration" refers to acceleration in any direction that is parallel to the plane that is generally defined by the piezoelectric sensor element 424. The overall length of the connecting rod 422 can influence the moment arm and, therefore, the amount of torque experienced by the piezoelectric sensor element 424 in response to parallel acceleration. Similarly, the adjustable height of the proof mass 420 along the connecting rod 422 represents another parameter of the accelerometer device 404 that can be tuned for parallel acceleration sensitivity. Moreover, the weight or mass of the proof mass 420 is another tunable parameter of the accelerometer device 404 that affects the parallel acceleration sensitivity (the weight/mass of the proof mass 420 also influences the perpendicular or axial acceleration sensitivity of the accelerometer device 404).

As another example, the dimensions and/or other electromechanical characteristics of the mass-supporting arms 442 could be varied (if desired) to adjust the sensitivity of the accelerometer device relative to different directions or axes. In this regard, the piezoelectric sensor element 424 depicted in FIG. 9 could be tuned such that the two vertical mass-supporting arms 442 are smaller than the two horizontal mass-supporting arms 442. With such tuning, the piezoelectric sensor element 424 will be more sensitive to acceleration in the vertical direction and less sensitive to acceleration in the horizontal direction. Likewise, the stiffness (e.g., the modulus of elasticity) of the piezoelectric sensor element 424 or the individual mass-supporting arms 442 can be adjusted or selected as desired to influence the sensitivity of the accelerometer device 404.

The dimensions, shape, and size of the sensor electrodes 440 and the underlying piezoelectric material also plays an important role in tuning the sensitivity of the accelerometer device 404. The electromechanical characteristics and properties of the sensor electrodes 440 and piezoelectric material can be tuned or designated to make the accelerometer device 404 more or less responsive to acceleration, and/or to adjust the directional sensitivity of the accelerometer device 404 as needed. For example, the longitudinal sensor length of each sensor electrode 440 along its respective mass-supporting arm 442 can be tuned in accordance with a predetermined perpendicular (axial) acceleration sensitivity for the accelerometer device 404. As used here, "perpendicular acceleration" refers to an acceleration component that is parallel to the longitudinal axis of the connecting rod 422. Referring to FIG. 9, the perpendicular acceleration component will be in the direction into and out of the page.

Monolithic Omnidirectional Accelerometer Device—Signal Processing

When the accelerometer device 404 is subjected to acceleration perpendicular to the plane of the piezoelectric sensor element 424, the proof mass 420 pushes or pulls on the mass-supporting platform 444, causing the four mass-supporting arms 442 to flex so as to produce a counterforce equal to the force that results from the acceleration. The amount of flexing of the mass-supporting arms 442 is thus proportional to the amount of acceleration experienced by the proof mass 420. When the accelerometer device 404 is subjected to acceleration parallel to the plane of the piezoelectric sensor element 424, the proof mass 420 rotates about its attachment point at the mass-supporting platform 444. This causes the mass-supporting arms 442 to flex so as to produce a counter torque equal to the torque caused by the moment arm of the connecting rod 422 and the force caused by acceleration of the proof mass 420. Therefore, the rotation of the mass-supporting arms 442 is proportional to the acceleration experienced by the proof mass 420 modified by the length of the moment arm associated with the connecting rod 422. Notably, acceleration of the host device in any direction will produce some mechanical distortion of at least one of the four mass-supporting arms 442.

Figure 10:
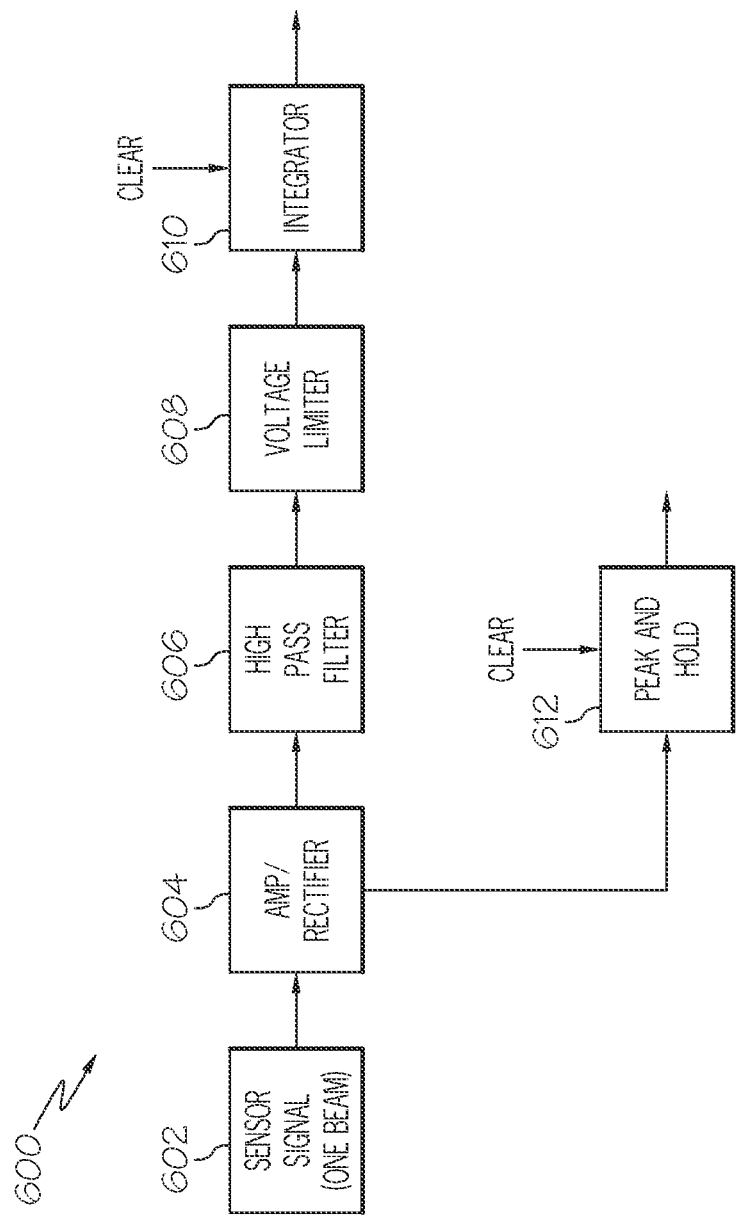
FIG. 10 is a schematic representation of an exemplary embodiment of an accelerometer signal processing module.

As described above with reference to FIG. 3, the output of the accelerometer can be processed by the accelerometer signal processing module 312. In this regard, FIG. 10 is a schematic representation of an exemplary embodiment of an accelerometer signal processing module 600, which is suitable for use with an accelerometer-enabled medical device. The accelerometer signal processing module 600 may be described herein in terms of functional and/or logical block components, and with reference to symbolic representations of operations, processing tasks, and functions that may be performed by electronic circuits, components, computing components, or devices.

The illustrated embodiment of the accelerometer signal processing module 600 includes, without limitation: a sensor signal input element 602; an amplifier/rectifier 604; a high pass filter 606; a voltage limiter 608; an integrator 610; and a peak and hold circuit 612. The elements shown in FIG. 10 are utilized to process the sensor signal from one of the four independent sensor electrodes 440 of the accelerometer device 404. In practice, therefore, the accelerometer signal processing module 600 may include four instantiations of the architecture shown in FIG. 10 (one instantiation per sensor electrode 440). Moreover, the accelerometer signal processing module 600 can concurrently process sensor signals in parallel for all of the sensor electrodes 440.

The accelerometer signal processing module 600 may be implemented as two sub-modules, which may be coupled in parallel to the sensor electrodes 440 of the accelerometer device. This allows the sub-modules to operate concurrently in parallel and to respond to the accelerometer sensor signals in the manner described here. The first sub-module is responsible for monitoring and detecting relatively low impact physical activity of the user, and the second sub-module is responsible for monitoring and detecting relatively high impacts experienced by the host device. The first sub-module includes the sensor signal input element 602, the amplifier/rectifier 604, the high pass filter 606, the voltage limiter 608, and the integrator 610. The second sub-module includes the sensor signal input element 602, the amplifier/rectifier 604, and the peak and hold circuit 612. The first sub-module processes the sensor signals for purposes of human activity monitoring, and the second sub-module processes the sensor signals for purposes of impact detection.

The sensor signal input element 602 obtains the sensor signal voltage from the respective sensor electrode 440, and the amplifier/rectifier 604 generates an amplified representation of the positive voltage portions of the input voltage signal. The negative voltage components are ignored or disregarded by the accelerometer signal processing module 600 because the voltage waveform is approximately symmetric (i.e., a negative voltage spike follows a positive voltage spike of approximately the same magnitude) as the proof mass settles.

The high pass filter 606 is designed to remove any DC offset and low frequency components of the rectified signal. In practice, the cutoff frequency of the high pass filter 606 can be set at about two Hertz, since the slowest human activity (e.g., walking) typically has a frequency that exceeds two Hertz. The high pass filter 606 ensures that a single step of the user produces only one voltage spike. The voltage limiter 608 limits the voltage of the filtered signal such that high impact spikes are disregarded. This allows the first sub-module to focus on typical human activity monitoring (walking, running, jogging). The output of the voltage limiter 608 is then fed to the integrator 610, which is used to sum or accumulate voltage or charge over time. In certain embodiments, the integrator 610 is realized using one or more analog capacitors, which are desirable for low power applications. The capacitor(s) accumulate the charge/voltage over a designated period of time (e.g., one to five minutes), which results in a stepped function that increases over time. This type of accumulation is preferred so that the accumulated charge/voltage can be preserved even when the main processor is asleep or in a standby mode.

After the designated time period has elapsed, the output of the integrator 610 is sent to another processor or controller element of the host device, and the integrator 610 can be cleared. For example, the output of the integrator 610 could be sent to the accelerometer response module 314 (see FIG. 3) or to the main processor of the host device. The accumulated voltage can thereafter be analyzed to determine a level of physical activity for that time period, for example, the number of steps taken per minute. The host device can then take appropriate action if needed. For example, the host device could recommend an adjustment to the user's infusion parameters, it could suggest the intake of calories, or it could recommend an insulin bolus.

For the second sub-module, the rectified signal is routed to the peak and hold circuit 612. The peak and hold circuit 612 is suitably configured to detect high impact spikes or pulses in the rectified signal. This embodiment of the peak and hold circuit 612 updates and holds the peak voltage level for a predetermined period of time. After the designated time period has elapsed, the output of the peak and hold circuit 612 is provided to another processor or controller element of the host device, and the peak and hold circuit 612 can be cleared. For example, the output of the peak and hold circuit 612 can be sent to the accelerometer response module 314 (see FIG. 3) or to the main processor of the host device. The peak voltage can thereafter be compared to one or more threshold levels to determine whether the host device was subjected to a high impact and, if so, to what extent. The host device can then take appropriate action if needed. For example, the host device could generate an alert or notification if it detects a high impact, or it could recommend a service inspection, or it could automatically send a self-diagnosis report to the manufacturer of the host device.

Accelerometer-Based Medical Device User Interface Features

Figure 11:
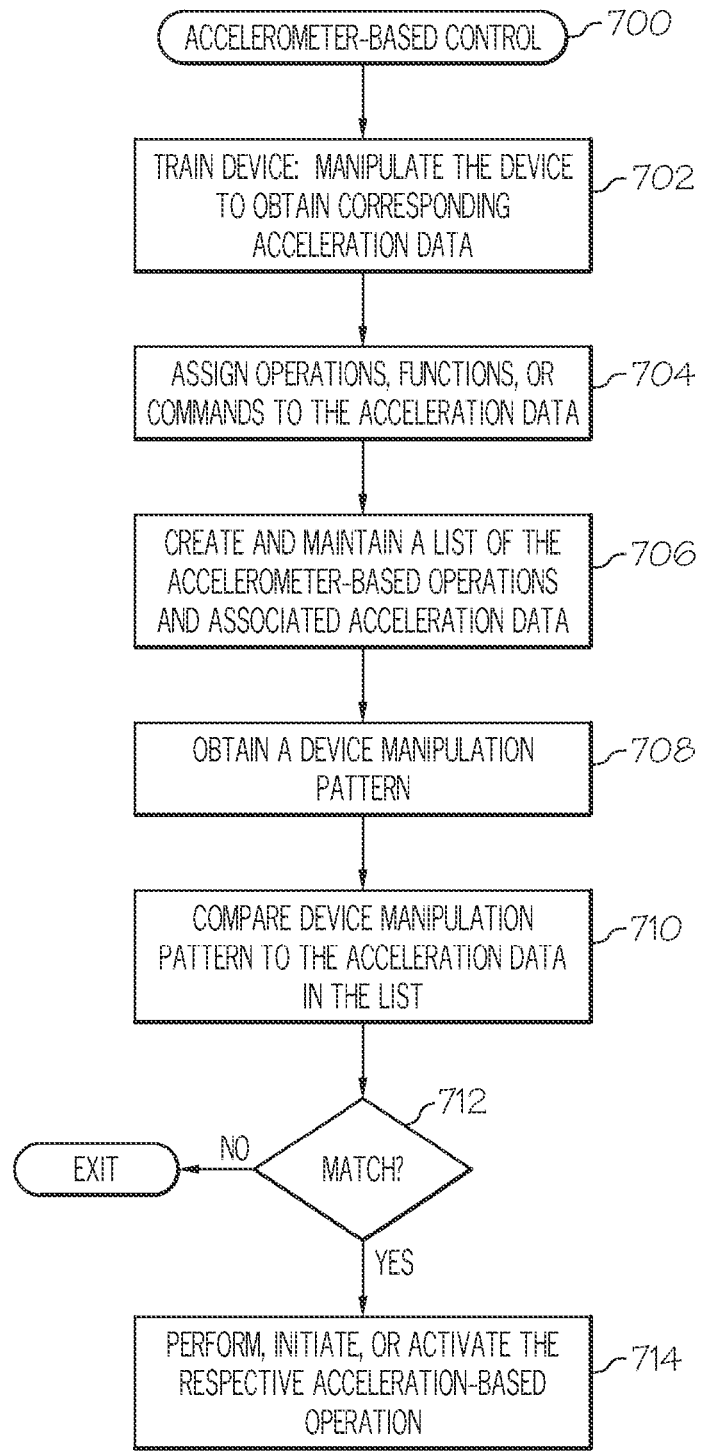
FIG. 11 is a flow chart that illustrates an embodiment of an accelerometer-based control process suitable for use with a portable medical device.

A medical device as described herein may be suitably configured to support one or more operations that are controlled, commanded, or otherwise influenced by the output of an onboard accelerometer. Such accelerometer-based functions may involve, for example, the accelerometer device 310, the accelerometer signal processing module 312, and the accelerometer response module 314 (see FIG. 3). In this regard, FIG. 11 is a flow chart that illustrates an embodiment of an accelerometer-based control process 700 suitable for use with a portable medical device. It should be appreciated that process 700 may include any number of additional or alternative tasks, the tasks shown in FIG. 11 need not be performed in the illustrated order, and process 700 may be incorporated into a more comprehensive procedure or process having additional functionality not described in detail herein. Moreover, an implementation of process 700 need not always perform all of the tasks shown in FIG. 11, and one or more of the illustrated tasks could be omitted (if the overall operation and functionality of process 700 is maintained).

The illustrated embodiment of process 700 includes several tasks that are related to the setup and initialization of the medical device. For example, the medical device may need to be trained before it can carry out accelerometer-linked operations. In this regard, a user can train the medical device by physically manipulating the device in a desired pattern (task 702) to obtain corresponding acceleration data, which can be recorded or saved. The process 700 can then assign (task 704) certain operations, functions, or commands to respective acceleration data. Thereafter, process 700 can create and maintain (task 706) an appropriate list of accelerometer-based operations, along with their associated acceleration data. This list of accelerometer-based operations can be stored and maintained in the local memory element of the medical device.

Task 704 can assign the operations in any desired manner. For example, after recording a particular manipulation pattern, task 704 could allow the user to select an operation that will be linked to that particular manipulation pattern. A manipulation pattern is any detectable movement, impact, motion, gesture, sequence of movements, or the like, where the manipulation pattern can be detected by the onboard accelerometer device. In this regard, one manipulation pattern might be a sequence of vertical shakes, while another manipulation pattern might be a sequence of horizontal taps on the housing of the device. Yet another manipulation pattern might be one shake (in any direction) followed by two quick shakes. Another manipulation pattern might be linked to a gesture or an imaginary path of motion for the device. It should be appreciated that the specific form, type, and/or mode of manipulation may vary, and that the number of different manipulation patterns need not be limited in any way. For example, a manipulation pattern of three up-and-down shakes of the device could be associated with a command to display the main menu of the device, and a different manipulation pattern of two shakes in rapid succession could be associated with a command to activate a backlight on the display. In practice, the list of accelerometer-based operations could contain any number of different operations, each being associated with a different manipulation pattern.

Although a medical device could be suitably configured to support any number of different accelerometer-initiated operations, the embodiments described here could maintain a list that contains therapy delivery operations linked to certain manipulation patterns, a list that contains display setting operations linked to respective manipulation patterns, and/or a list that contains menu selection operations linked to respective manipulation patterns. Different therapy delivery operations cause the medical device to deliver or administer different types or amounts of therapy to the patient (via the medical device itself or via a therapy delivery device under the control of the medical device). For example, one designated manipulation pattern might be used to initiate the delivery of a first dosage of insulin, and another manipulation pattern might initiate the delivery of a second dosage of insulin. A display setting operation may cause the medical device to display a respective visual display, e.g., a chart, a graph, or the like. Thus, different modes of accelerometer excitation, movement patterns, shaking patterns, or motions can be used to switch the display of the medical device. A menu selection operation may cause the medical device to display a respective menu, e.g., the home menu, a settings menu, a therapy programming menu, or the like. Thus, commonly used menus can be linked to certain manipulation patterns to facilitate quick switching of menu screens.

After the medical device has been trained with recorded acceleration data, the process 700 can be used to initiate or activate the accelerometer-based operations in response to user manipulation of the device. For example, the medical device can obtain a device manipulation pattern (task 708) using the onboard accelerometer. The obtained device manipulation pattern data can then be analyzed to compare it to identifiable acceleration data maintained in the list of accelerometer-based operations (task 710). If the detected manipulation pattern satisfies certain matching criteria (query task 712) for saved acceleration data, then process 700 can perform, initiate, or activate the respective acceleration-based operation (task 714). The operation could be activated at the medical device itself or, if the medical device is a remote controller, then the remote controller could wirelessly transmit a control message to the device under its control—upon receipt of the control message, the receiving device can then execute the designated operation. If, however, the detected manipulation pattern data does not match any of the previously trained acceleration data, then process 700 may present an error message or simply exit without taking any action.

Accelerometer-Based Medical Device Therapy Adaptation

One or more accelerometer devices onboard a wearable medical device could also be used to estimate physical activity of the user and, in response to the estimated physical activity, adapt at least one therapy-related function or feature of the medical device. As described above with reference to FIG. 10, physical activity could be monitored by processing the output of an omnidirectional accelerometer device and/or the outputs of a plurality of accelerometer devices. In certain embodiments, the positive portion of the accelerometer output signal(s) is integrated to obtain a more accurate estimate of the calories burned by the user during the monitored period of time. In this regard, if the user is walking at a quick pace, then there will be more accelerometer output voltage spikes or pulses per unit of time. If the user is doing high impact exercise, then each accelerometer output voltage spike or pulse will be of higher magnitude, resulting in more area to be integrated during the processing of the output signal. Thus, the use of one or more accelerometers allows the medical device to determine whether the user has been running, walking, going uphill, going downhill, jumping, etc. Estimating calories burned in this manner is more accurate than the traditional technique of simply counting steps.

The manner in which the medical device calculates a measure of energy expended per unit of time (e.g., calories) may vary from one device or application to another. For example, the accelerometer output signals could be processed using an electronic circuit implementation and/or using a software-implemented algorithm or program. After a measure of energy expended per unit of time (e.g., calories) has been calculated, the medical device can make corresponding adjustments. For example, it may be desirable to adjust one or more parameters related to the delivery of therapy and/or to provide recommendations to the user. In an insulin infusion system, the accelerometer data could be used to adjust the basal rate of insulin, to recommend a bolus dosage, or the like.

The output of an accelerometer could also be used to automatically switch a therapy delivery device from a closed loop mode to an open loop mode (and vice versa). For example, if the accelerometer output indicates no physical activity for an extended period of time, then the medical device might assume that the user is asleep and, therefore, automatically activate or maintain a closed loop monitoring and therapy delivery mode. This is desirable so that the device can continue to monitor the user and administer therapy if needed even if the user is sleeping. On the other hand, if the accelerometer output detects at least some physical activity over a designated period of time, then the medical device might assume that the user is awake and, therefore, automatically activate or maintain an open loop monitoring and therapy delivery mode. Open loop operation is desirable when the user is awake so that the user retains control over certain functions, such as the delivery of therapy.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An omnidirectional accelerometer device comprising:
   a piezoelectric sensor element comprising a mass-supporting platform and a plurality of mass-supporting arms for a plurality of electrically distinct sensor electrodes, each of the mass-supporting arms extending from a central bore defined in the mass-supporting platform, and each of the mass-supporting arms having one of the sensor electrodes formed thereon;
   a connecting rod having a mounting end, a mass end, and a longitudinal length defined between the mounting end and the mass end, the mounting end being coupled to the mass-supporting platform such that the connecting rod passes through the central bore;
   a conductive offset block coupled to a perimeter of the mass supporting platform of the piezoelectric sensor element so as to be positioned between the piezoelectric sensor element and a circuit board, the offset block sized such that the mounting end of the connecting rod is spaced apart from the circuit board; and
   a proof mass coupled to the mass end of the connecting rod, wherein acceleration of the proof mass causes deflection of the mass-supporting arms, which generates distinct sensor signals at the sensor electrodes; wherein:
   the longitudinal length of the connecting rod is tuned in accordance with a predetermined parallel acceleration sensitivity for the omnidirectional accelerometer device;
   each of the sensor electrodes has a longitudinal sensor length along its respective mass-supporting arm; and
   the longitudinal sensor length is tuned in accordance with a predetermined perpendicular acceleration sensitivity for the omnidirectional accelerometer device.

2. The omnidirectional accelerometer device of claim 1, wherein the piezoelectric sensor element comprises:
   an electrically conductive support substrate;
   a layer of piezoelectric material overlying the support substrate; and
   the sensor electrodes overlying the piezoelectric material, the sensor electrodes being formed from an electrically conductive material.

3. The omnidirectional accelerometer device of claim 2, wherein: the electrically conductive support substrate provides a reference voltage; and each of the sensor electrodes provides a respective sensor signal voltage.

4. The omnidirectional accelerometer device of claim 1, wherein:
   the mass-supporting arms are symmetrically positioned relative to the central bore.

5. The omnidirectional accelerometer device of claim 1, wherein adjacent mass-supporting arms are orthogonal.

6. The omnidirectional accelerometer device of claim 1, wherein adjacent mass-supporting arms define a separation angle for the piezoelectric sensor element.

7. The omnidirectional accelerometer device of claim 1, wherein a height of the proof mass relative to the mass-supporting platform is adjustable to tune the omnidirectional accelerometer device in accordance with the predetermined parallel acceleration sensitivity.

8. The omnidirectional accelerometer device of claim 7, wherein the connecting rod further comprises a threaded bolt.

9. The omnidirectional accelerometer device of claim 8, wherein the proof mass is adjustable along the threaded bolt to a desired height.

10. The omnidirectional accelerometer device of claim 9, wherein the proof mass further comprises a threaded hole for threadably engaging the threaded bolt of the connecting rod to adjustably couple the proof mass to the connecting rod.

11. An omnidirectional accelerometer device comprising:
a piezoelectric sensor element comprising a mass-supporting platform and a plurality of mass-supporting arms for a plurality of electrically distinct sensor electrodes, each of the mass-supporting arms extending from a central bore defined in the mass-supporting platform, and each of the mass-supporting arms having one of the sensor electrodes formed thereon;
a connecting rod having a mounting end, a mass end, and a longitudinal length defined between the mounting end and the mass end, the mounting end being coupled to the mass-supporting platform such that the connecting rod passes through the central bore;
a conductive offset block coupled to a perimeter of the mass supporting platform of the piezoelectric sensor element so as to be positioned between the piezoelectric sensor element and a circuit board, the offset block sized such that the mounting end of the connecting rod is spaced apart from the circuit board; and
a proof mass coupled to the mass end of the connecting rod and adjustable along the longitudinal length of the connecting rod to tune the omnidirectional accelerometer device in accordance with a predetermined parallel acceleration sensitivity,
wherein acceleration of the proof mass causes deflection of the mass-supporting arms, which generates distinct sensor signals at the sensor electrodes.

12. The omnidirectional accelerometer device of claim 11, wherein:
the mass-supporting arms are symmetrically positioned relative to the central bore.

13. The omnidirectional accelerometer device of claim 12, mounting end of the connecting rod is coupled to the mass supporting platform such that the longitudinal length and mass end of the connecting rod extends through the central bore.

14. The omnidirectional accelerometer device of claim 11, wherein adjacent mass-supporting arms are orthogonal.

15. The omnidirectional accelerometer device of claim 11, wherein the connecting rod further comprises a threaded bolt.

16. The omnidirectional accelerometer device of claim 15, wherein the proof mass further comprises a threaded hole for threadably engaging the threaded bolt of the connecting rod to adjustably couple the proof mass to the connecting rod.

17. The omnidirectional accelerometer device of claim 11, wherein the longitudinal length of the connecting rod is tuned in accordance with the predetermined parallel acceleration sensitivity for the omnidirectional accelerometer device.

18. The omnidirectional accelerometer device of claim 11, wherein each of the sensor electrodes has a longitudinal sensor length along its respective mass-supporting arm, and the longitudinal sensor length is tuned in accordance with a predetermined perpendicular acceleration sensitivity for the omnidirectional accelerometer device.

19. The omnidirectional accelerometer device of claim 11, wherein the piezoelectric sensor element comprises:
an electrically conductive support substrate;
a layer of piezoelectric material overlying the support substrate; and
the sensor electrodes overlying the piezoelectric material, the sensor electrodes being formed from an electrically conductive material.

20. The omnidirectional accelerometer device of claim 19, wherein: the electrically conductive support substrate provides a reference voltage; and each of the sensor electrodes provides a respective sensor signal voltage.

* * * * *